US 11,821,841 B2

(12) United States Patent
Pandey et al.

(10) Patent No.: US 11,821,841 B2
(45) Date of Patent: Nov. 21, 2023

(54) SYSTEM AND METHOD FOR CLASSIFICATION OF TISSUE BASED ON RAMAN AND FLUORESCENCE IN HIGH-WAVENUMBER RAMAN SPECTRUM

(71) Applicant: CytoVeris Inc., Farmington, CT (US)

(72) Inventors: Rishikesh Pandey, Unionville, CT (US); Alan Kersey, South Glastonbury, CT (US)

(73) Assignee: CytoVeris, Inc., Farmington, CT (US)

( * ) Notice: Subject to any disclaimer, the term of this patent is extended or adjusted under 35 U.S.C. 154(b) by 0 days.

(21) Appl. No.: 17/688,792

(22) Filed: Mar. 7, 2022

(65) Prior Publication Data

US 2022/0283093 A1 Sep. 8, 2022

Related U.S. Application Data

(60) Provisional application No. 63/157,357, filed on Mar. 5, 2021, provisional application No. 63/157,344, filed on Mar. 5, 2021.

(51) Int. Cl.
*G01N 21/65* (2006.01)
*G01N 21/64* (2006.01)
*A61B 5/00* (2006.01)

(52) U.S. Cl.
CPC ......... *G01N 21/65* (2013.01); *G01N 21/6486* (2013.01); *A61B 5/0075* (2013.01)

(58) Field of Classification Search
None
See application file for complete search history.

(56) References Cited

U.S. PATENT DOCUMENTS

| | | | |
|---|---|---|---|
| 7,499,153 B2 | 3/2009 | Puppels | |
| 8,326,404 B2 | 12/2012 | Zeng | |
| 2019/0117078 A1* | 4/2019 | Sharma | A61B 1/24 |

FOREIGN PATENT DOCUMENTS

| | | | | |
|---|---|---|---|---|
| WO | 2014147416 A1 | 9/2014 | | |
| WO | WO-2014147416 A1 * | 9/2014 | | G01J 3/027 |

OTHER PUBLICATIONS

Gebrekidan, M. T., et al. "A shifted-excitation Raman difference spectroscopy (SERDS) evaluation strategy for the efficient isolation of Raman spectra from extreme fluorescence interference." Journal of Raman spectroscopy 47.2 (2016): 198-209 (Year: 2016).*

(Continued)

*Primary Examiner* — Tarifur R Chowdhury
*Assistant Examiner* — Roberto Fabian, Jr.
(74) *Attorney, Agent, or Firm* — Getz Balich LLC (57) ABSTRACT

A method and system for classifying a tissue specimen is provided. The method includes: a) interrogating a tissue specimen with a first interrogation light; b) detecting first light from the tissue specimen resulting from the interrogation, wherein the first light includes a first scattered light component and a first fluorescence light component, and producing first signals; c) interrogating the tissue specimen with a second interrogation light at a second excitation wavelength, wherein the first and second excitation wavelengths are within about 2 nm of each other; d) detecting second light from the tissue specimen resulting from the interrogation, wherein the second light includes a second scattered light component and a second fluorescence light component, and producing second signals; e) determining a difference between the first and second lights; f) determining a fluorescence spectrum produced by the interrogation of the tissue specimen; and g) classifying the tissue specimen.

18 Claims, 7 Drawing Sheets

(56) References Cited

OTHER PUBLICATIONS

A. S. Haka, et al., "In vivo margin assessment during partial mastectomy breast surgery using Raman spectroscopy," Cancer Res. 66(6), 3317-3322 (2006).

Aubertin et al., "Combining high wavenumber and fingerprint Raman spectroscopy for the detection of prostate cancer during radical prostatectomy", 9, (9), Biomedical Optics Express, p. 4294, (2018).

Gebrekidan et al., A shifted-excitation Raman difference spectroscopy (SERDS) evaluation strategy for the efficient isolation of Raman spectra from extreme fluorescence interference, J. Raman Spectrosc., 47: 198-209 (2016).

J. Mo, et al., "High wavenumber Raman spectroscopy for in vivo detection of cervical dysplasia," Anal. Chem. 81(21), 8908-8915(2009).

K. Lin, et al., "Optical diagnosis of laryngeal cancer using high wavenumber Raman spectroscopy," Biosens. Bioelectron. 35(1), 213-217 (2012).

Pandey et al. "Raman spectroscopy based molecular bar coding: realizing the value of high wavenumber region in breast cancer detection", Proc. SPIE 11631, Advanced Biomedical and Clinical Diagnostic and Surgical Guidance Systems XIX, 1163105 (Mar. 5, 2021); https://doi.org/10.1117/12.2578933.

Wang et al., "Simultaneous fingerprint and high-wavenumber fiber-optic Raman spectroscopy improves in vivo diagnosis of esophageal squamous cell carcinoma at endoscopy", Scientific Reports, 5, Article No. 12957 (2015).

\* cited by examiner

SYSTEM AND METHOD FOR CLASSIFICATION OF TISSUE BASED ON RAMAN AND FLUORESCENCE IN HIGH-WAVENUMBER RAMAN SPECTRUM

This application claims priority to U.S. Patent Application No. 63/157,344 filed Mar. 5, 2021, and to U.S. Patent Application No. 63/157,357 filed Mar. 5, 2021, both of which are hereby incorporated by reference in their entirety.

BACKGROUND OF THE INVENTION

1. Technical Area

The present disclosure relates to systems and methods for examining a biological samples using Raman spectroscopy and fluorescence characteristics derived from Raman spectra in general, and more specifically to such systems and methods operating in the high wavenumber region in particular.

2. Background Information

Raman spectrum of interest in biological sample analysis includes two primary regions of interest: the "Fingerprint" or "FP" region and the "High Wavenumber" or "HWN" region. The FP region typically includes a wavenumber range of about 400 $cm^{-1}$ to about 1800 $cm^{-1}$ and the HWN region typically includes a wavenumber range of about 2800 $cm^{-1}$ to about 3800 $cm^{-1}$. The FP region typically comprises a series of multiple peaks and is rich in Raman spectral information. In the case of biological samples, the FP region contains information on the relative content of biomolecular components, such as DNA, proteins, phospholipids, lipids, and the like. Research based on the FP region alone has demonstrated the detection of cancerous tissue [1]. The HWN region typically includes a composite broad spectral shape that includes several underlying peaks associated with different biomolecules. Recent work in the HWN range has demonstrated successful classification of cancerous tissue versus normal tissue with high sensitivity and specificity [2-6]. The Raman spectral features from tissue in HWN are typically unaffected by Raman signals from glass as well as from tissue marking dye. It has been shown that combining information from the FP and HWN regions can lead to enhanced performance for some applications [7]. A molecular barcoding approach discerning tissues types in the HWN region has also been reported [8]. In the FP region where there is a higher amount of fluorescence, some applications are understood to use two slightly shifted excitation wavelengths to acquire two Raman spectra consecutively at the same spatial location on the tissue and remove confounding background tissue fluorescence [9]. The combination of Raman and autofluorescence features have been utilized for tissue analysis previously [5, 10].

SUMMARY OF THE INVENTION

According to an aspect of the present disclosure, a method for classifying a tissue specimen as a type of tissue is provided. The method includes: a) interrogating a tissue specimen with a first interrogation light at a first excitation wavelength; b) detecting first light from the tissue specimen resulting from the interrogation of the tissue specimen with the first interrogation light, wherein the first light includes a first scattered light component and a first fluorescence light component, and producing first signals representative of the first light thereof; c) interrogating the tissue specimen with a second interrogation light at a second excitation wavelength, wherein the second excitation wavelength is within about 2 nm of the first excitation wavelength; d) detecting second light from the tissue specimen resulting from the interrogation of the tissue specimen with the second interrogation light, wherein the second light includes a second scattered light component and a second fluorescence light component, and producing second signals representative thereof; e) determining a difference between the first light and the second light using the first signals and the second signals; f) determining a fluorescence spectrum produced by the interrogation of the tissue specimen with at least one of the first interrogation light or the second interrogation light; and g) classifying the tissue specimen as a type of tissue using the determined difference and the determined fluorescence spectrum.

In any of the aspects or embodiments described above and herein, the step of determining a difference between the first light and the second light may include determining a Raman spectrum difference.

In any of the aspects or embodiments described above and herein, the first fluorescence light component and the second fluorescence light component may cancel each other out in the step of determining a Raman spectrum difference.

In any of the aspects or embodiments described above and herein, the step of determining a fluorescence spectrum may include using the Raman spectrum difference.

In any of the aspects or embodiments described above and herein, the step of classifying the tissue specimen may utilize the fluorescence spectrum.

In any of the aspects or embodiments described above and herein, the step of classifying the tissue specimen may utilize a classifier having stored data representative of fluorescence emissions and scattered light from different said types of tissue.

In any of the aspects or embodiments described above and herein, the step of classifying the tissue specimen may utilize a classifier that uses machine learning or artificial intelligence and an empirical data set based on fluorescence emissions and Raman scattering from an acceptably sized training set of reference tissue samples.

In any of the aspects or embodiments described above and herein, at least a portion of the first light and at least a portion of the second light may be used to determine the fluorescence spectrum and may be used to determine a Raman spectrum difference.

In any of the aspects or embodiments described above and herein, the first scattered light component and the first fluorescence light component may be acquired simultaneously, and the second scattered light component and the second fluorescence light component may be acquired simultaneously.

In any of the aspects or embodiments described above and herein, the first scattered light component and the first fluorescence light component may be acquired simultaneously as a result of the interrogation of the tissue specimen with the first interrogation light at the first excitation wavelength, and the second scattered light component and the second fluorescence light component may be acquired simultaneously as a result of the interrogation of the tissue specimen with the second interrogation light at the second excitation wavelength.

According to another aspect of the present disclosure, a system for classifying a tissue specimen as a type of tissue is provided that includes at least one light source, a spectrometer, at least one light detector, and a system controller.

The system controller is in communication with the at least one light source, the at least one light detector, and a non-transitory memory storing instructions. The instructions when executed cause the system controller to: a) control the at least one light source to interrogate a tissue specimen with a first interrogation light at a first excitation wavelength; b) control the at least one light detector to detect first light from the tissue specimen resulting from the interrogation of the tissue specimen with the first interrogation light, wherein the first light includes a first scattered light component and a first fluorescence light component, and produce first signals representative of the first light thereof; c) control the at least one light source to interrogate the tissue specimen with a second interrogation light at a second excitation wavelength, wherein the second excitation wavelength is within about 2 nm of the first excitation wavelength; d) control the at least one light detector to detect second light from the tissue specimen resulting from the interrogation of the tissue specimen with the second interrogation light, wherein the second light includes a second scattered light component and a second fluorescence light component, and producing second signals representative thereof; e) determine a difference between the first light and the second light using the first signals and the second signals; f) determine a fluorescence spectrum produced by the interrogation of the tissue specimen with at least one of the first interrogation light or the second interrogation light; and g) classify the tissue specimen as a type of tissue using the determined difference and the determined fluorescence spectrum.

In any of the aspects or embodiments described above and herein, wherein the determination of the difference between the first light and the second light may include determining a Raman spectrum difference.

In any of the aspects or embodiments described above and herein, wherein the determination of the fluorescence spectrum may include using the Raman spectrum difference.

In any of the aspects or embodiments described above and herein, wherein the classification of the tissue specimen may utilize the fluorescence spectrum.

In any of the aspects or embodiments described above and herein, wherein the classification may utilize a classifier having stored data representative of fluorescence emissions and scattered light from different said types of tissue.

In any of the aspects or embodiments described above and herein, wherein the classification may utilize a classifier that utilizes machine learning or artificial intelligence and an empirical data set based on fluorescence emissions and Raman scattering from an acceptably sized training set of reference tissue samples.

In any of the aspects or embodiments described above and herein, wherein the instructions when executed may use at least a portion of the first light and at least a portion of the second light to determine the fluorescence spectrum and to determine a Raman spectrum difference between the first scattered light component and the second scattered light component.

In any of the aspects or embodiments described above and herein, the instructions when executed may cause the system controller to produce a plurality of Raman bar codes for the tissue specimen, with each Raman bar code based on a ratio of peak wavenumber intensities.

In any of the aspects or embodiments described above and herein, the tissue type classification of the tissue specimen may be is based at least in part on one or more of the Raman bar codes.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

DETAILED DISCLOSURE

Figure 1:
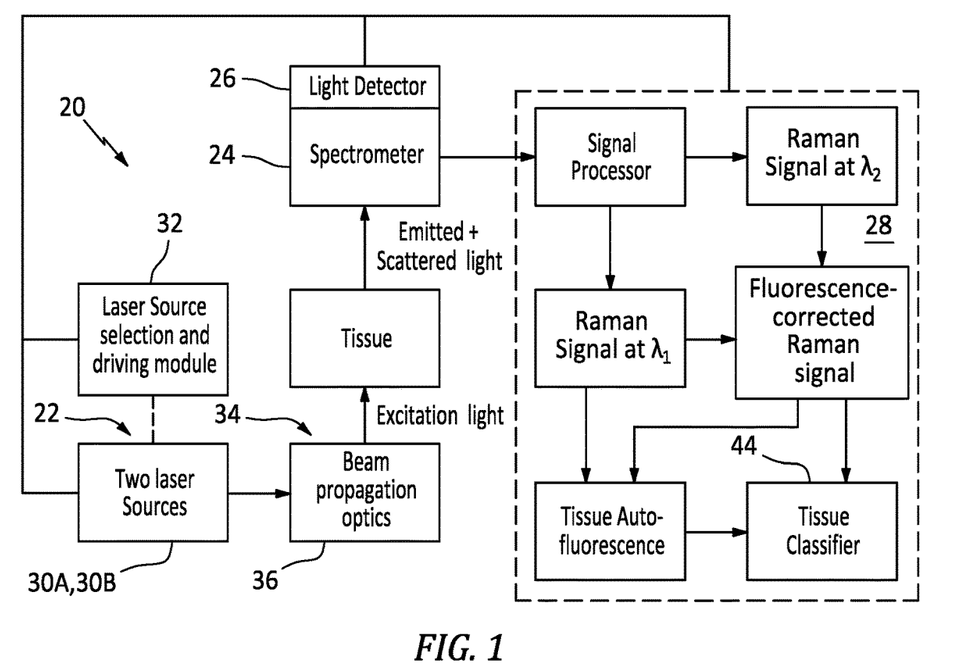
FIG. 1 is a diagrammatic representation of a present disclosure system embodiment.
Figure 2:
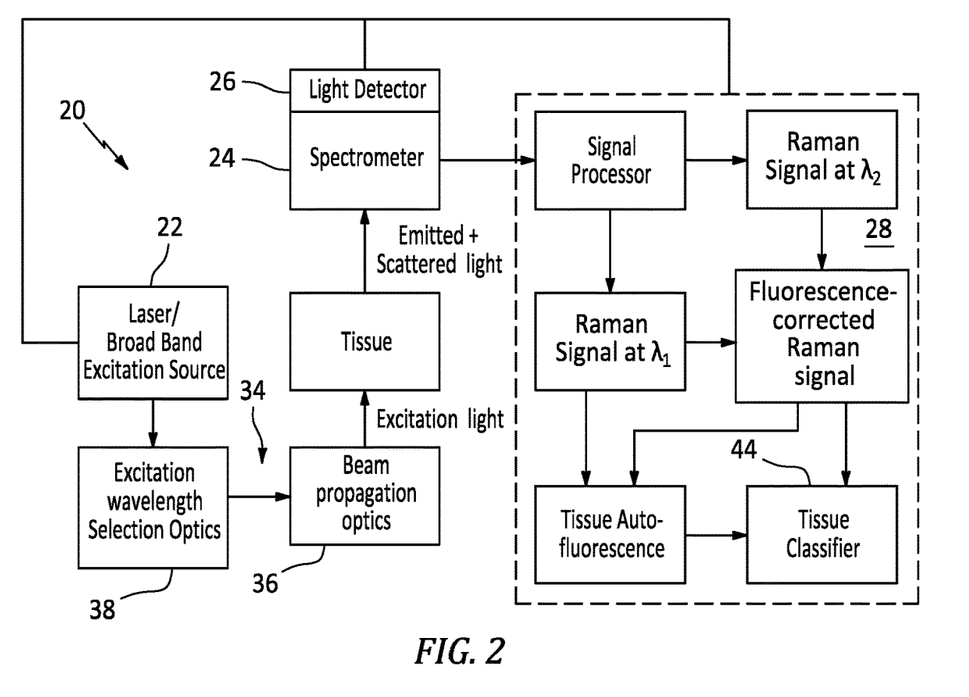
FIG. 2 is a diagrammatic representation of a present disclosure system embodiment.
Figure 3:
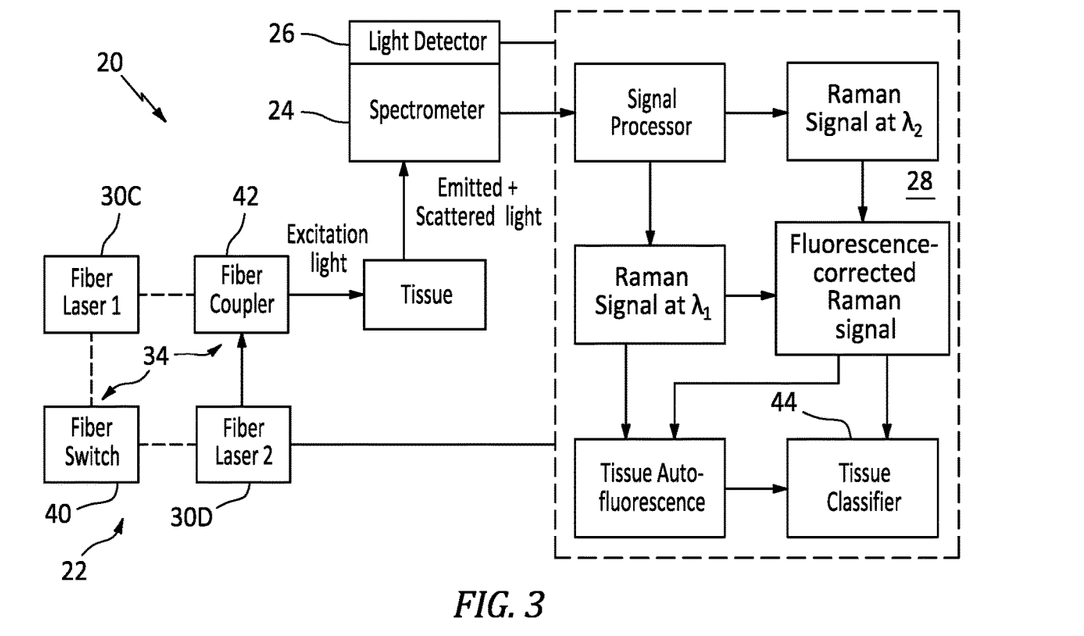
FIG. 3 is a diagrammatic representation of a present disclosure system embodiment.

Referring to FIGS. 1-3, the present disclosure includes a method and system for automated classification of tissue based on Raman spectra and autofluorescence in the high wavenumber region of the Raman spectrum. Embodiments of the present disclosure system 20 may include a light source 22, a spectrometer 24, a light detector 26, and a system controller 28.

The light source 22 is configured to emit light at a plurality of wavelengths that will produce Raman spectra in the HWN region when interrogating a tissue specimen. The present disclosure may use a variety of different light source 22 types and is not limited to any particular type of light source 22. Non-limiting examples of acceptable laser that may be used, for example, include solid state, gas, diode laser or vertical-cavity surface-emitting lasers (VCSELs). The present disclosure system 20 diagrammatically shown in FIG. 1 includes a pair of lasers 30A, 30B and a laser source selection and driving module 32. The present disclosure system 20 diagrammatically shown in FIG. 2 includes a light source 22 that is a single source of light such as a broad-band light source that may be filtered, or a tunable laser, or the like. The present disclosure system 20 diagrammatically shown in FIG. 3 includes a pair of lasers 30C, 30D. These are non-limited examples of light source 22 types and configurations that may be utilized. The present disclosure may utilize light for excitation/interrogation purposes at a variety of different wavelengths, and the light source 22 is therefore not limited to producing light at any particular wavelength or wavelength band.

In some embodiments, a present disclosure system 20 may include optical elements 34 operable to form or otherwise manage the light produced by the light source 22. For example, the present disclosure system 20 shown in FIG. 1 includes beam propagation optics 36, the system 20 shown in FIG. 2 includes excitation wavelength selection optics 38 and beam propagation optics 36, and the system 20 shown in FIG. 3 includes a fiber switch 40 and a fiber coupler 42. These are non-limited examples of optical elements 34 operable to form and/or manage the light that is used to interrogate the tissue sample and the present disclosure is not limited thereto.

Embodiments of the present disclosure may include a spectrometer 24 (or a monochromator, or the like—collectively referred to herein as a "spectrometer 24" to facilitate the description) coupled with a light detector 26. The spectrometer 24 may be configured to receive and process light emitted from the tissue (e.g., fluorescent emissions) and scattered light emanating from the tissue as a result of the tissue being interrogated with light from the light source 22. The light detector 26 receives the processed light spectrum from the spectrometer 24, produces signals representative thereof, and communicates those signals to the system controller 28. Non-limiting examples of a light detector 26 type that may be used include a light sensor that converts light energy into an electrical signal such as a camera, a simple photodiode, a CCD array, or the like.

The system controller 28 is in communication with other system components such as the light source 22, the light detector 26, and the like. In some embodiments, the system controller 28 may be in communication with any one of the spectrometer 24, the light source 22, optical elements 34, the laser source selection and driving module 34, a tissue classifier 44 (which may be internal to the system controller 28), and other system components, and any combination thereof. The system controller 28 may be in communication with these components to control the operation of the respective component and/or to receive signals from and/or transmit signals to that component to perform the functions described herein. The system controller 28 may include any type of computing device, computational circuit, processor(s), CPU, computer, or the like capable of executing a series of instructions that are stored in memory. The instructions may include an operating system, and/or executable software modules such as program files, system data, buffers, drivers, utilities, and the like. The executable instructions may apply to any functionality described herein to enable the system 20 to accomplish the same algorithmically and/or coordination of system components. The system controller 28 includes or is in communication with one or more memory devices. The present disclosure is not limited to any particular type of memory device, and the memory device may store instructions and/or data in a non-transitory manner. Examples of memory devices that may be used include read-only memory, random access memory, volatile memory, non-volatile memory, static memory, dynamic memory, flash memory, cache memory, and/or any device that stores digital information. The system controller 28 may include, or may be in communication with, an input device that enables a user to enter data and/or instructions, and may include, or be in communication with, an output device configured, for example to display information (e.g., a visual display or a printer), or to transfer data, etc. Communications between the system controller 28 and other system components may be via a hardwire connection or via a wireless connection.

The present disclosure provides a novel and advantageous tissue classification method that utilizes Raman spectra obtained using differential excitations and the use of complementary spectral information contents. The present approach utilizes sequential acquisitions of Raman spectra produced at slightly shifted excitation wavelengths (e.g., about <2 nm). The Raman spectra produced by the shifted excitation wavelengths includes a fluorescence-free Raman spectra component and likely includes a fluorescence component. Since fluorescence is generally independent of the excitation wavelength, the fluorescence component of the Raman spectra produced at the two excitation wavelengths remains the substantially the same while the fluorescence-free Raman spectra component of the excitation produced Raman spectrum shifts according to the excitation wavelength. A difference between the two produced Raman spectrum is determined and is subsequently used to remove the fluorescence component of the shifted excitation produced Raman spectrum, thereby producing a fluorescence-free Raman difference spectrum. The fluorescence-free Raman difference spectrum may then be used in conjunction with one or both of the original Raman spectrums to identify the fluorescence spectrum (i.e., the fluorescence component) produced in the HWN region. The separated Raman spectra and the fluorescence spectrum in the HWN region may then be used for tissue classification purposes. In addition, the fluorescence-free Raman spectrum and the fluorescence spectrum may be used to develop a classifier by integrating the emission and scattering characteristics of the tissue. The Raman difference spectrum may be generated, for example, using a variety of different mathematical techniques including subtraction or weighted subtraction, and may include baseline correction, smoothing, etc. In some embodiments, reconstruction techniques may be used to achieve accurate Raman profiles. Fluorescence-free Raman signal may be generated using a reconstruction of a Raman difference spectrum. A non-limiting example of a reconstruction process is zero-centered reconstruction. In some cases, a machine learning based approach might be utilized to generate and process the Raman difference spectrum.

Hence, the present disclosure utilizes otherwise confounding fluorescence attributes (i.e., the fluorescence component of the Raman spectra produced at the two excitation wavelengths) and combines them with information-rich fluorescence-free Raman features in the HWN region for tissue analysis. Importantly, no separate fluorescence measurements are performed, and the fluorescence attributes are derived from Raman spectra produced at the two excitation wavelengths. Typically, Raman spectroscopy measurements of tissue are performed in near infra-red (NIR) region to leverage the lower contribution of background autofluorescence in the NIR region of the Raman spectrum. The present disclosure, in contrast, acquires Raman scattered light signals produced by excitation wavelengths in the visible region and therefore allows increased Raman signals due to the known $1/\lambda^4$ dependence of Raman signal with the excitation wavelength.

Importantly, the present disclosure allows the recording of the Raman spectrum from tissue with visible/UV excitation providing a higher Raman cross-section and tissue autofluorescence. The present disclosure approach is different from conventional bimodal Raman and fluorescence detection systems and provides several advantages. For example, the fluorescence-free Raman component and the fluorescence component of the Raman spectra produced at each excitation wavelength are acquired simultaneously from the same system with the same illumination and collection optics ensuring no registration error and sample perturbation. As another example, both the modalities use the same excitation wavelengths, and therefore the illumination and observation volumes are the same. Still further, the fluorescence in the HWN region determinable using the present disclosure is free from fluorescence contribution from tissue marking dyes (which does not directly provide any tissue information), and therefore primarily encompasses intrinsic tissue fluorescence (which may provide tissue information).

Figure 4:
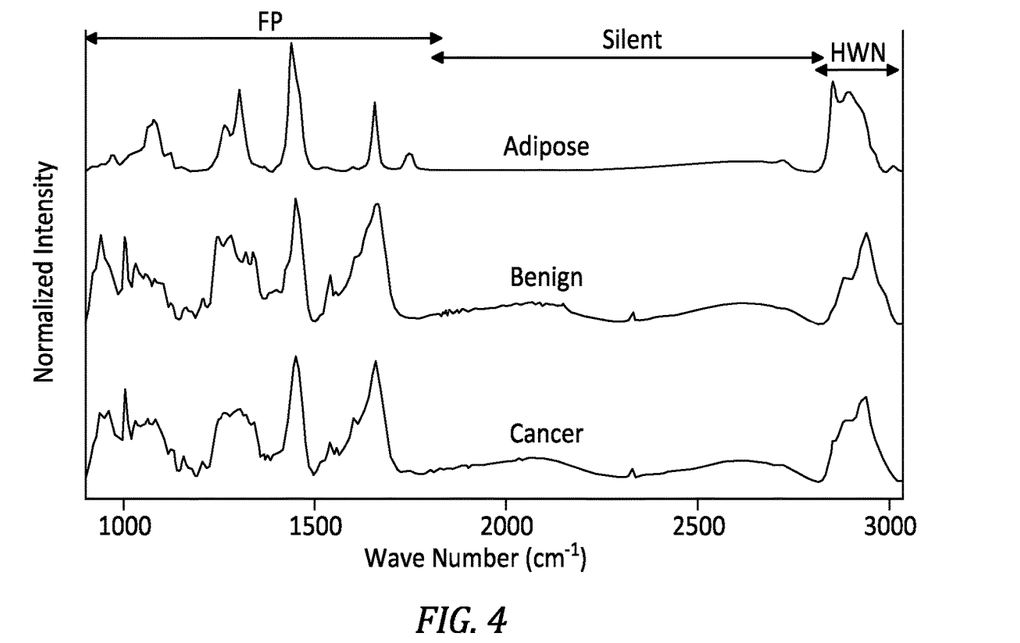
FIG. 4 is a graph of exemplary representative Raman spectra of three major breast tissues showing different regions.
Figure 5:
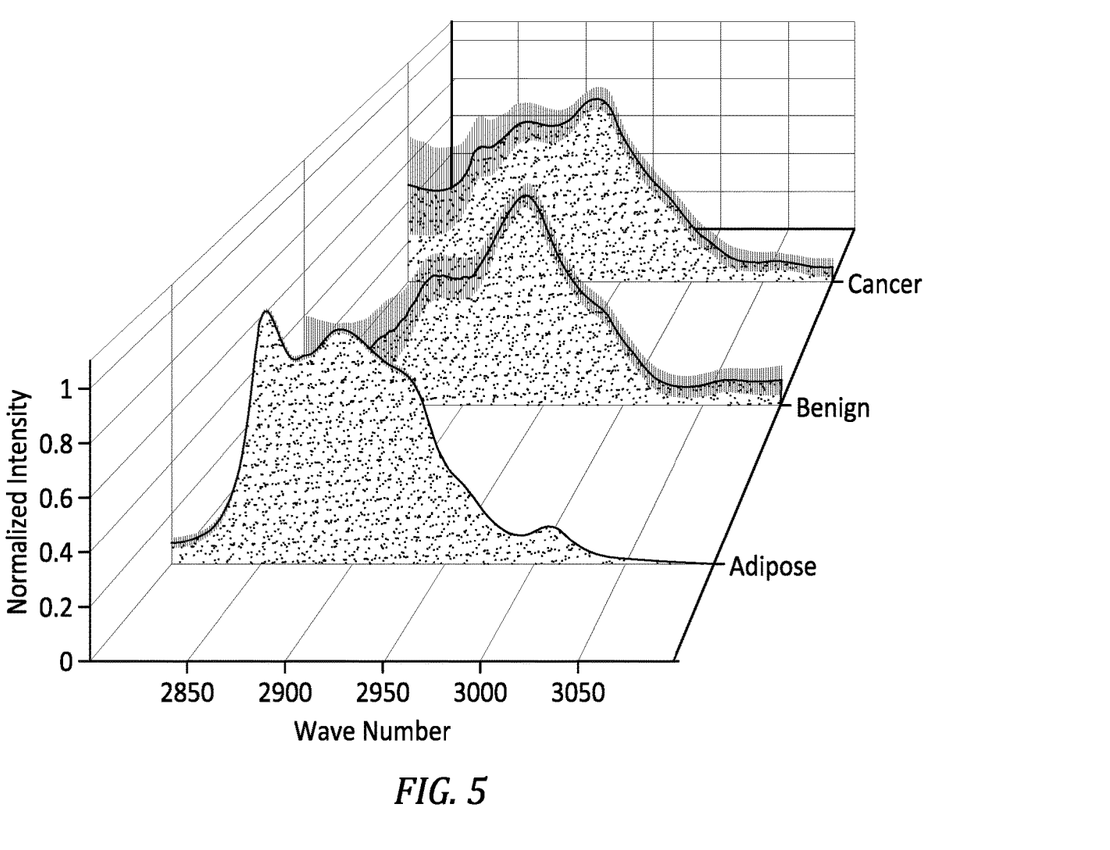
FIG. 5 is a graph of Raman spectra illustrating normalized intensity on the Y-axis and wavenumbers on the X-axis.

The intensity versus wavenumber curves shown in FIG. 4 illustrate representative Raman spectrum for adipose, benign and cancer human breast tissues within the fingerprint ("FP") region (e.g., about 400 cm' to about 1800 $cm^{-1}$), the silent region (e.g., about 1800 $cm^{-1}$ to about 2800 $cm^{-1}$), and the high wavenumber ("HWN") region (e.g., about 2800 cm' to about 3800 $cm^{-1}$). FIG. 5 graphically illustrates rich Raman features in the HWN region which are used by the present disclosure for tissue analysis/classification. The graph of normalized intensity versus wavenumber in the HWN region shown in FIG. 5 includes curves representative of Raman spectrum data collected from sensing a statistically significant number of tissue specimens; e.g., adipose, benign, and cancer tissues. The term "statistically significant" as used herein means that a sufficient amount of data is collected to produce a clinically reasonable confidence level that the data is accurate and representative.

Figure 6:
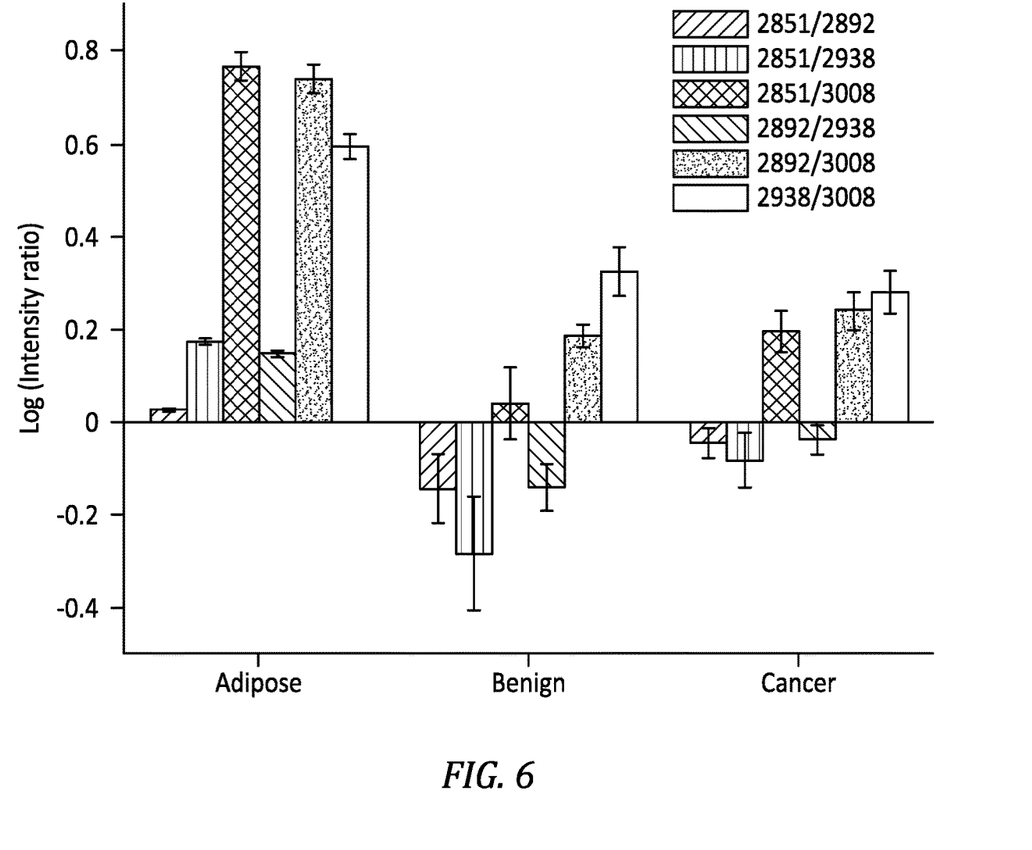
FIG. 6 is a graph of Raman intensity ratios for adipose, benign tissue, and cancerous tissue with log intensity ratios on the Y-axis for and for each of the adipose, benign tissue, and cancerous tissue types on the X-axis.

FIG. 6 graphically illustrates a panel of six (6) mean peak wavenumber intensity ratios (e.g., A=2851 $cm^{-1}$/2892 $cm^{-1}$; B=2851 $cm^{-1}$/2938 $cm^{-1}$; C=2851 $cm^{-1}$/3008 $cm^{-1}$; D=2892 $cm^{-1}$/2938 $cm^{-1}$; E=2892 $cm^{-1}$/3008 $cm^{-1}$; and F=2938 $cm^{-1}$/3008 $cm^{-1}$) that may be used to generate distinct barcodes for different types of breast tissues. The intensity ratios of selected peaks are shown as bars in the graph of FIG. 6 and the related standard deviation of the measurements are shown in FIG. 6 as a linear line centrally located with each bar. The ratios shown in FIG. 6 illustrate examples of mean peak wavenumber intensity ratios that may be useful in tissue analysis, but the present disclosure is not limited to these particular ratios or the indicated wavenumbers. Different mean peak wavenumber intensity ratios may be used for different applications. In addition, the present disclosure is not limited to using six (6) ratios; fewer or more mean peak wavenumber intensity ratios may be used alternatively. The six (6) mean peak wavenumber ratios chosen to illustrate herein are based on four (4) HWN peaks: (a) 2851 $cm^{-1}$, ascribed to C—H vibrations of CH2 and primarily attributable to lipid content, (b) 2938 $cm^{-1}$, mainly ascribed to C—H vibrations of CH3 group which reflect predominantly the protein content; (c) 2892 $cm^{-1}$, corresponding to CH2 asymmetric stretch of both proteins and lipids; and (d) 3008 $cm^{-1}$, representing =C—H vibration associated with the lipids and fatty acids.

Figure 7:
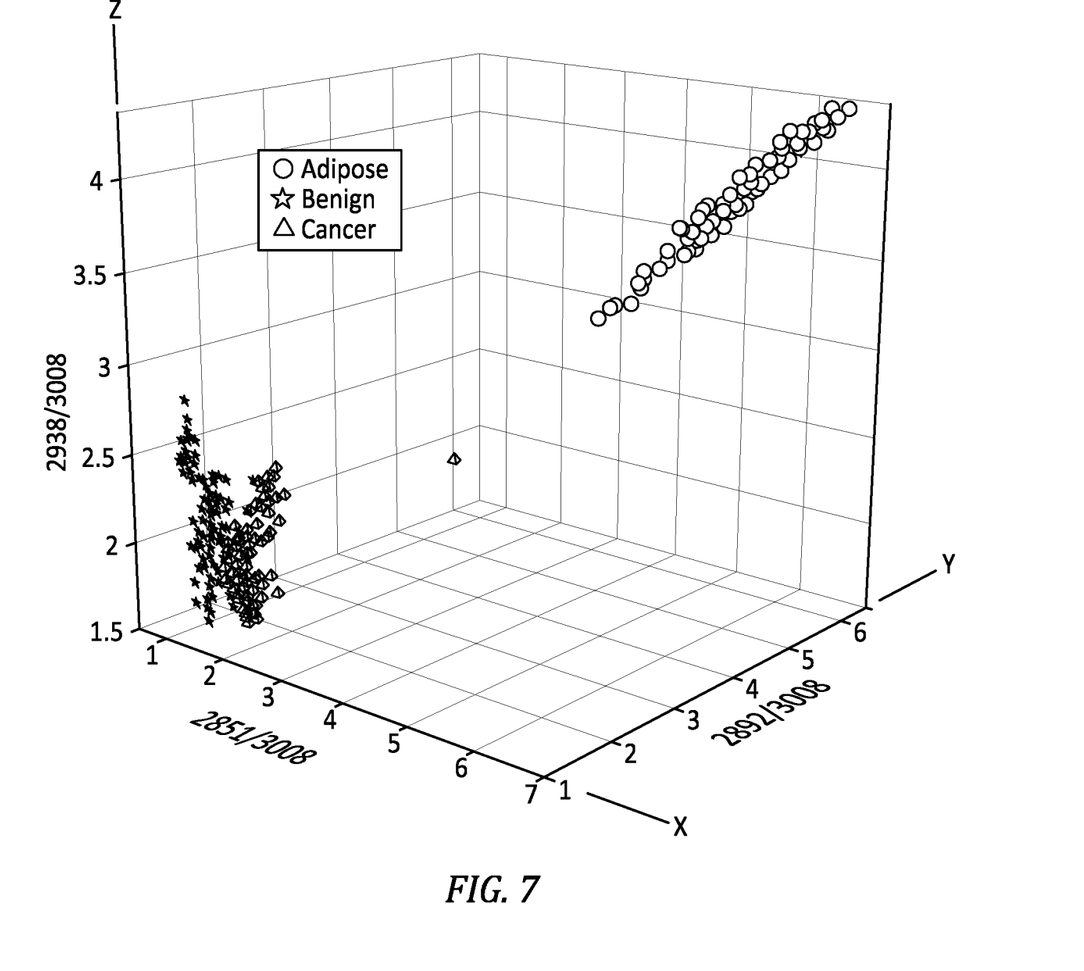
FIG. 7 is a three-dimensional plot of three exemplary intensity ratios, each intensity ratio assigned an orthogonal axis, illustrating clustering of sensed tissue specimen data.
Figure 8:
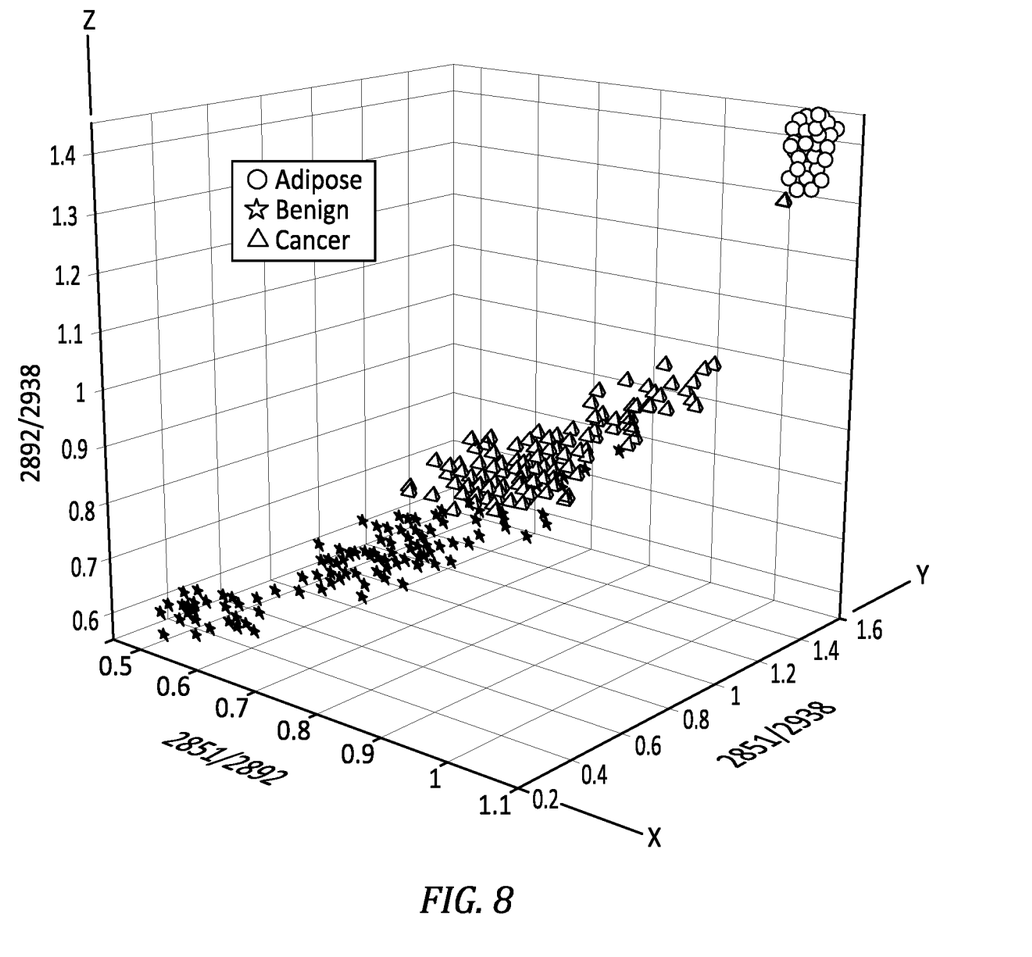
FIG. 8 is a three-dimensional plot of three exemplary intensity ratios, each intensity ratio assigned an orthogonal axis, illustrating clustering of sensed tissue specimen data.

FIG. 7 is a three dimensional (3D) plot having three (3) mean peak wavenumber intensity ratio axes to illustrate sensed data clustering of different tissues (e.g., adipose, benign, and cancerous) based on the three mean peak wavenumber intensity ratios (i.e., 2938 $cm^{-1}$/3008 $cm^{-1}$ on a Z-axis, 2851 $cm^{-1}$/3008 $cm^{-1}$ on an X-axis, and 2982 $cm^{-1}$/3008 $cm^{-1}$ on a Y-axis). As is shown in FIG. 7, there is perceptible separation within the sensed data for the three tissue types. FIG. 8 is a similar 3D plot utilizing three different mean peak wavenumber intensity ratios (i.e., 2892 $cm^{-1}$/2938 $cm^{-1}$ on a Z-axis, 2851 $cm^{-1}$/2892 $cm^{-1}$ on an X-axis, and 2851 $cm^{-1}$/2938 $cm^{-1}$ on a Y-axis). Here again, there is perceptible separation within the sensed data for the three tissue types.

Referring back to FIGS. 1-3, the operation of these exemplary system 20 embodiments will now be described in greater detail to facilitate understanding of the present disclosure. Each of these system 20 embodiments utilizes Raman and fluorescence signals obtained using differential wavelength excitations and the use of complementary spectral information contents.

The system 20 embodiment shown in FIG. 1 includes a laser source selection and driving module 32 that is operable to control a light source 22 having a first laser 30A and a second laser 30B; e.g., the laser source selection and driving module 32 is operable (e.g., via instructions stored in the system controller 28) to select one of the first and second lasers 30A, 30B to operate, and then controls that laser to produce a light beam centered on a wavelength. Subsequently, the laser source selection and driving module 32 is operated to select the other of the first and second lasers 30A, 30B to operate, and then controls that laser to produce a light beam centered on a wavelength. Hence, the laser source selection and driving module 32 operates the lasers 30A, 30B in an alternating manner. For purposes of this description, we may assume that one of the lasers is configured to produced light centered on a first wavelength ($\lambda_1$) and the other laser is configured to produced light centered on a second wavelength ($\lambda_2$). The system 20 embodiment shown in FIG. 2 includes a light source 22 that has a single source of light such as a broad-band light source 22 that may be filtered to produced desired excitation wavelengths ($\lambda_1$, $\lambda_2$) or a tunable laser that can be tuned (e.g., via instructions stored in the system controller 28) to produce the desired excitation wavelengths ($\lambda_1$, $\lambda_2$). The system 20 embodiment shown in FIG. 3 includes a light source 22 that includes a first laser 30C and a second laser 30D, both of which may be fiber lasers or lasers in communication with fiber optics. The first and second lasers 30C, 30D are in communication with a fiber switch 40 and a fiber coupler 42. The fiber switch 40 is operable (e.g., via instructions stored in the system controller 28) to switch operation of the first and second lasers 30C, 30D. The fiber coupler 42 is operable to couple the output from each of the first and second lasers (30A, 30B—$\lambda_1$, $\lambda_2$) into a single path to the tissue sample. Any of the exemplary system 20 embodiments may include optical elements 34 beyond those shown in the Figures for the purpose of forming/managing the produced light. For example, controllable optical elements 34 may be used to manipulate the light point of incidence on the sample.

The light sequentially produced from the light source 22 ($\lambda_1$, $\lambda_2$) is directed to the tissue specimen. The incident light at each wavelength produces Raman spectra (comprising the fluorescence-free Raman component and the fluorescence component). The Raman spectra produced at each excitation wavelength is received and processed by the spectrometer 24 and detected by the light detector 26. The light detector 26 produces signals representative of the detected light and communicates those signals to the system controller 28. The system 20 embodiment examples shown in FIGS. 1-3 diagrammatically illustrate the processing of the signals received at the system controller 28; e.g., sequential acquisition of Raman spectra (comprising the fluorescence-free Raman component and the fluorescence component); the fluorescence component of the Raman spectra is removed using a difference between the two produced Raman spectrum and a fluorescence-free Raman difference spectrum is determined; the fluorescence-free Raman difference spectrum may then be used in conjunction with one or both of the original Raman spectrums to identify the fluorescence spectrum produced in the HWN region; and the separated Raman spectra and the fluorescence spectrum in the HWN region may then be used to for tissue classification purposes, including developing a classifier by integrating the fluorescence emission and Raman scattered light characteristics of the tissue relative to particular excitation wavelengths, as well as classifying specific tissue specimens. In some embodiments, the classifier may be based on/utilize machine learning or artificial intelligence utilizing an empirical data set; e.g., empirical data based on fluorescence emissions and Raman scattering from an acceptably sized training set of reference tissue samples.

Figure 9:
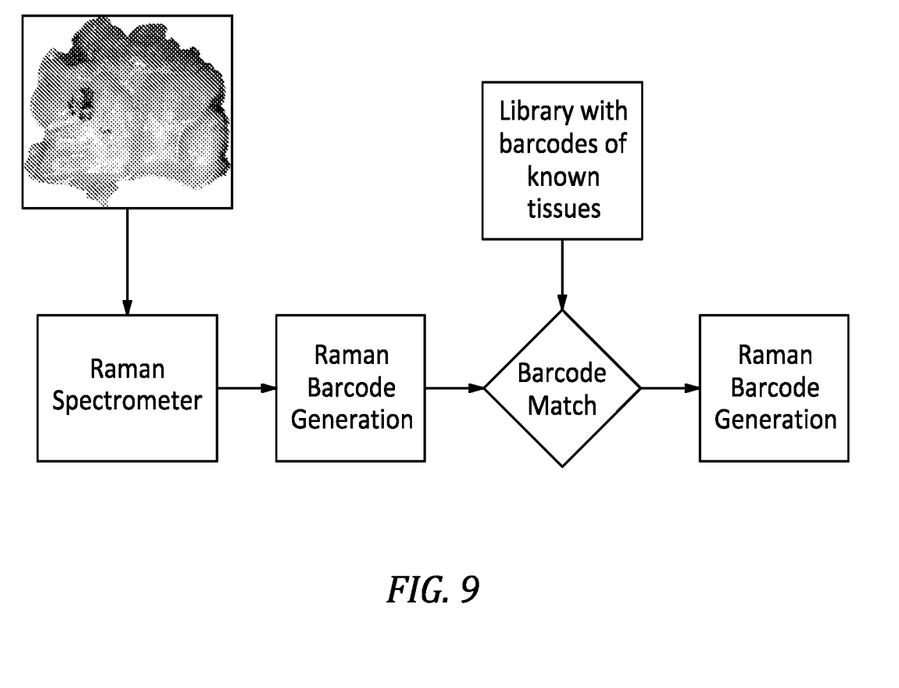
FIG. 9 is a schematic illustration of a classification approach embodiment using Raman Bar Coding (RBC).

FIG. 9 is a schematic diagram of an exemplary classification approach using Raman Bar Coding (RBC) that may be utilized within the present disclosure. The Raman spectra acquired in HWN region (e.g., the wavenumber ratio data shown in FIG. 6) may be processed algorithmically to generate RBCs for a given tissue specimen. The RBCs associated with the tissue specimen may then be classified using RBCs stored in a memory device (e.g., in a data base format or the like), which stored RBCs are representative of different tissue types. This type of RBC classification can be used to determine the tissue specimen type or to identity a tissue type outlier for further analysis.

In some present disclosure embodiments, the fluorescence emissions may be used in conjunction with the "Spectrometer-less Multiplexed Detection Approach for High Wavenumber Raman Scattering Based Classification of Normal and Diseased Tissue" as described in U.S. Patent Application No. 63/055,987 and PCT Patent Application No. PCT/US2021/043196, both of which are assigned to the present applicant and hereby incorporated by reference in their respective entirety, and/or the peak fitting concepts described in U.S. Patent Application No. 63/157,357 filed Mar. 5, 2021 to which the present application claims priority, and to U.S. patent application Ser. No. 17/688,776 filed concurrently herewith and which is hereby incorporated by reference in its entirety. For instance, the molecular barcoding (e.g., see FIG. 6) that utilizes intensity ratios can have an additional value such as peak area, peak width, etc. These non-limiting examples could utilize maximum intensity of the retrieved fluorescence spectrum and the area under the peak. In some embodiments, fluorescence spectrum feature(s) may be utilized in a barcode analysis.

While the principles of the disclosure have been described above in connection with specific apparatuses and methods, it is to be clearly understood that this description is made only by way of example and not as limitation on the scope of the disclosure. Specific details are given in the above description to provide a thorough understanding of the embodiments. However, it is understood that the embodiments may be practiced without these specific details.

It is noted that the embodiments may be described as a process which is depicted as a flowchart, a flow diagram, a block diagram, etc. Although any one of these structures may describe the operations as a sequential process, many of the operations can be performed in parallel or concurrently. In addition, the order of the operations may be rearranged. A process may correspond to a method, a function, a procedure, a subroutine, a subprogram, etc.

The singular forms "a," "an," and "the" refer to one or more than one, unless the context clearly dictates otherwise. For example, the term "comprising a specimen" includes single or plural specimens and is considered equivalent to the phrase "comprising at least one specimen." The term "or" refers to a single element of stated alternative elements or a combination of two or more elements unless the context clearly indicates otherwise. As used herein, "comprises" means "includes." Thus, "comprising A or B," means "including A or B, or A and B," without excluding additional elements.

It is noted that various connections are set forth between elements in the present description and drawings (the contents of which are included in this disclosure by way of reference). It is noted that these connections are general and, unless specified otherwise, may be direct or indirect and that this specification is not intended to be limiting in this respect. Any reference to attached, fixed, connected or the like may include permanent, removable, temporary, partial, full and/or any other possible attachment option.

No element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for." As used herein, the terms "comprise", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

While various inventive aspects, concepts and features of the disclosures may be described and illustrated herein as embodied in combination in the exemplary embodiments, these various aspects, concepts, and features may be used in many alternative embodiments, either individually or in various combinations and sub-combinations thereof. Unless expressly excluded herein all such combinations and sub-combinations are intended to be within the scope of the present application. Still further, while various alternative embodiments as to the various aspects, concepts, and features of the disclosures—such as alternative materials, structures, configurations, methods, devices, and components, and so on—may be described herein, such descriptions are not intended to be a complete or exhaustive list of available alternative embodiments, whether presently known or later developed. Those skilled in the art may readily adopt one or more of the inventive aspects, concepts, or features into additional embodiments and uses within the scope of the present application even if such embodiments are not expressly disclosed herein. For example, in the exemplary embodiments described above within the Detailed Description portion of the present specification, elements may be described as individual units and shown as independent of one another to facilitate the description. In alternative embodiments, such elements may be configured as combined elements.

REFERENCES

The following references are hereby incorporated by reference in their respective entireties:

1. A. S. Haka, et al., "In vivo margin assessment during partial mastectomy breast surgery using Raman spectroscopy," Cancer Res. 66(6), 3317-3322 (2006).
2. J. Mo, et al., "High wavenumber Raman spectroscopy for in vivo detection of cervical dysplasia," Anal. Chem. 81(21), 8908-8915 (2009).
3. K. Lin, et al., "Optical diagnosis of laryngeal cancer using high wavenumber Raman spectroscopy," Biosens. Bioelectron. 35(1), 213-217 (2012).
4. Aubertin et al., "Combining high wavenumber and fingerprint Raman spectroscopy for the detection of prostate cancer during radical prostatectomy", 9, (9), Biomedical Optics Express, p. 4294, (2018)

5. PCT Publication No. WO 2014/147416, Notingher et al., "Measurement of Tissue Structures".
6. U.S. Pat. No. 7,499,153 issued to Puppels et al., "Use of High Wavenumber Raman Spectroscopy for Measuring Tissue".
7. Wang et al., "Simultaneous fingerprint and high-wavenumber fiber-optic Raman spectroscopy improves in vivo diagnosis of esophageal squamous cell carcinoma at endoscopy, Scientific Reports, 5, Article number: 12957 (2015)
8. R. Pandey et al, "Raman spectroscopy based molecular barcoding: realizing the value of high wavenumber region in breast cancer detection", Proc. SPIE 11631, Advanced Biomedical and Clinical Diagnostic and Surgical Guidance Systems XIX, 1163105 (5 Mar. 2021).
9. Gebrekidan et al., A shifted-excitation Raman difference spectroscopy (SERDS) evaluation strategy for the efficient isolation of Raman spectra from extreme fluorescence interference, J. Raman Spectrosc., 47: 198-209 (2016)
10. U.S. Pat. No. 8,326,404 issued to Zeng et al., "Multimodal Detection of Tissue Abnormalities based on Raman and Background Fluorescence Spectroscopy".

The invention claimed is:

1. A method for classifying a tissue specimen as a type of tissue, comprising:
   interrogating a tissue specimen with a first interrogation light at a first excitation wavelength;
   detecting first light from the tissue specimen resulting from the interrogation of the tissue specimen with the first interrogation light, wherein the first light includes a first scattered light component and a first fluorescence light component, and producing first signals representative of the first light thereof;
   interrogating the tissue specimen with a second interrogation light at a second excitation wavelength, wherein the second excitation wavelength is within about 2 nm of the first excitation wavelength;
   detecting second light from the tissue specimen resulting from the interrogation of the tissue specimen with the second interrogation light, wherein the second light includes a second scattered light component and a second fluorescence light component, and producing second signals representative thereof;
   determining a Raman spectrum difference between the first light and the second light using the first signals and the second signals;
   determining a fluorescence spectrum produced by the interrogation of the tissue specimen with at least one of the first interrogation light or the second interrogation light; and
   classifying the tissue specimen as a type of tissue using the determined Raman spectrum difference and the determined fluorescence spectrum.

2. The method of claim 1, wherein the step of determining said fluorescence spectrum includes using the Raman spectrum difference.

3. The method of claim 1, wherein the step of classifying the tissue specimen utilizes the fluorescence spectrum.

4. The method of claim 1, wherein the step of classifying the tissue specimen utilizes a classifier having stored data representative of fluorescence emissions and scattered light from different said types of tissue.

5. The method of claim 1, wherein the step of classifying the tissue specimen utilizes a classifier utilizing machine learning or artificial intelligence and an empirical data set based on fluorescence emissions and Raman scattering from an acceptably sized training set of reference tissue samples.

6. The method of claim 1, wherein at least a portion of the first light and at least a portion of the second light is used to determine the fluorescence spectrum and is used to determine a Raman spectrum difference.

7. The method of claim 1, wherein the first scattered light component and the first fluorescence light component are acquired simultaneously, and the second scattered light component and the second fluorescence light component are acquired simultaneously.

8. The method of claim 1, wherein the first scattered light component and the first fluorescence light component are acquired simultaneously as a result of the interrogation of the tissue specimen with the first interrogation light at the first excitation wavelength, and the second scattered light component and the second fluorescence light component are acquired simultaneously as a result of the interrogation of the tissue specimen with the second interrogation light at the second excitation wavelength.

9. A system for classifying a tissue specimen as a type of tissue, comprising:
   at least one light source;
   a spectrometer;
   at least one light detector; and
   a system controller in communication with the at least one light source, the at least one light detector, and a non-transitory memory storing instructions, which instructions when executed cause the system controller to:
     control the at least one light source to interrogate a tissue specimen with a first interrogation light at a first excitation wavelength;
     control the at least one light detector to detect first light from the tissue specimen resulting from the interrogation of the tissue specimen with the first interrogation light, wherein the first light includes a first scattered light component and a first fluorescence light component, and produce first signals representative of the first light thereof;
     control the at least one light source to interrogate the tissue specimen with a second interrogation light at a second excitation wavelength, wherein the second excitation wavelength is within about 2 nm of the first excitation wavelength;
     control the at least one light detector to detect second light from the tissue specimen resulting from the interrogation of the tissue specimen with the second interrogation light, wherein the second light includes a second scattered light component and a second fluorescence light component, and producing second signals representative thereof;
     determine a Raman spectrum difference between the first light and the second light using the first signals and the second signals;
     determine a fluorescence spectrum produced by the interrogation of the tissue specimen with at least one of the first interrogation light or the second interrogation light; and
     classify the tissue specimen as a type of tissue using the determined Raman spectrum difference and the determined fluorescence spectrum.

10. The system of claim 9, wherein the determination of the fluorescence spectrum includes using the Raman spectrum difference.

11. The system of claim 9, wherein the classification of the tissue specimen utilizes the fluorescence spectrum.

12. The system of claim 9, wherein the classification utilizes a classifier having stored data representative of fluorescence emissions and scattered light from different said types of tissue.

13. The system of claim 9, wherein the classification utilizes a classifier that utilizes machine learning or artificial intelligence and an empirical data set based on fluorescence emissions and Raman scattering from an acceptably sized training set of reference tissue samples.

14. The system of claim 9, wherein the instructions when executed use at least a portion of the first light and at least a portion of the second light to determine the fluorescence spectrum and to determine a Raman spectrum difference.

15. The system of claim 9, wherein the first scattered light component and the first fluorescence light component of the first light are acquired simultaneously, and the second scattered light component and the second fluorescence light component of the second light are acquired simultaneously.

16. The system of claim 9, wherein the first scattered light component and the first fluorescence light component of the first light are acquired simultaneously as a result of the interrogation of the tissue specimen with the first interrogation light at the first excitation wavelength, and the second scattered light component and the second fluorescence light component of the second light are acquired simultaneously as a result of the interrogation of the tissue specimen with the second interrogation light at the second excitation wavelength.

17. The system of claim 9, wherein the instructions when executed cause the system controller to produce a plurality of Raman bar codes for said tissue specimen, each said Raman bar code based on a ratio of peak wavenumber intensities.

18. The system of claim 17, wherein the tissue type classification of the tissue specimen is based at least in part on one or more of said Raman bar codes.

* * * * *